(12) United States Patent
Taniguchi et al.

(10) Patent No.: US 7,385,198 B2
(45) Date of Patent: Jun. 10, 2008

(54) METHOD AND APPARATUS FOR MEASURING THE PHYSICAL PROPERTIES OF MICRO REGION

(75) Inventors: Yoshifumi Taniguchi, Hitachinaka (JP); Mikio Ichihashi, Nagoya (JP); Masanari Kouguchi, Kunitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/326,399

(22) Filed: Jan. 6, 2006

(65) Prior Publication Data

US 2006/0113473 A1 Jun. 1, 2006

Related U.S. Application Data

(62) Division of application No. 10/467,303, filed on Aug. 7, 2003, now Pat. No. 7,022,988.

(51) Int. Cl.
*H01J 37/26* (2006.01)
(52) U.S. Cl. .................... 250/310; 250/307
(58) Field of Classification Search ............ 250/307, 250/310
See application file for complete search history.

(56) References Cited

U.S. PATENT DOCUMENTS

| | | | |
|---|---|---|---|
| 5,004,918 A | 4/1991 | Tsuno et al. | |
| 5,414,261 A | 5/1995 | Ellisman et al. | |
| 5,502,306 A | 3/1996 | Meisburger et al. | |
| 5,552,602 A | 9/1996 | Kakibayashi et al. | |
| 5,578,821 A | 11/1996 | Meisberger et al. | |
| 5,650,621 A | 7/1997 | Tsuneta et al. | |
| 5,866,905 A | 2/1999 | Kakibayashi et al. | |
| 6,051,834 A | 4/2000 | Kakibayashi et al. | |
| 6,548,811 B1 | 4/2003 | Nakamura et al. | |
| 6,570,156 B1 | 5/2003 | Tsuneta et al. | |
| 6,750,451 B2 | 6/2004 | Koguchi et al. | |
| 6,852,974 B2 | 2/2005 | Kochi et al. | |
| 6,888,139 B2 * | 5/2005 | Tsuneta et al. ............. 250/311 |

FOREIGN PATENT DOCUMENTS

| | | |
|---|---|---|
| JP | 59-163548 | 9/1984 |
| JP | 02-079348 | 3/1990 |

(Continued)

OTHER PUBLICATIONS

Kimoto, et al.; "Measurement of Strain in Locally Oxidized Silicon Using Convergent-Beam Electron Diffraction." Jpn. J. Appl. Phys. vol. 32, Part 2, No. 2A, L211-213, Feb. 1, 1993.

*Primary Examiner*—David A. Vanore
(74) *Attorney, Agent, or Firm*—Dickstein Shapiro LLP

(57) ABSTRACT

A method and apparatus for measuring the physical properties of a micro region measures the two-dimensional distribution of stress/strain in real time at high resolution and sensitivity and with a high level of measuring position matching. A sample is scanned and irradiated with a finely focused electron beam (23, 26), and the displacement of position of a diffraction spot (32, 33) is measured by a two-dimensional position-sensitive electron detector (13). The displacement amount is outputted as a voltage value that is then converted into the magnitude of the stress/strain according to the principle of a nano diffraction method, and the magnitude is displayed in synchronism with a sample position signal.

11 Claims, 10 Drawing Sheets

FOREIGN PATENT DOCUMENTS

| | | |
|---|---|---|
| JP | 02-197050 | 8/1990 |
| JP | 02-220339 | 9/1990 |
| JP | 4-206941 | 7/1992 |
| JP | 05-087746 | 4/1993 |
| JP | 6-36729 | 2/1994 |
| JP | 7-282769 | 10/1995 |
| JP | 08-138609 | 5/1996 |
| JP | 09-097584 | 4/1997 |
| JP | 10-162768 | 6/1998 |
| JP | 2000-46762 | 2/2000 |
| JP | 2000-65762 | 3/2000 |
| JP | 2000-331637 | 11/2000 |

* cited by examiner

METHOD AND APPARATUS FOR MEASURING THE PHYSICAL PROPERTIES OF MICRO REGION

CROSS-REFERENCE TO RELATED APPLICATION

This application is a divisional of U.S. patent application No. 10/467,303, filed on Aug. 7, 2003 now U.S. Pat. No. 7,022,988, the subject matter of which is hereby incorporated by reference in its entirety.

TECHNICAL FIELD

The present invention relates to a method and apparatus for measuring physical properties of a micro region of a sample. Particularly, it relates to a micro-region physical property measuring method and apparatus whereby local strain or stress in a sample is measured by means of the displacement of a particular spot position of an electron beam diffraction image.

BACKGROUND ART

Stresses and strains that are created in a metallic material, for example, during machining are one of the important design factors that determine the reliability of not only the components manufactured from the material but also the final products assembled from the components. In the field of semiconductor apparatuses, device sizes are becoming increasingly smaller, and the defective current leak property due to changes in electron states or the presence of micro defects at the interface caused by residual stress or concentrated strain is becoming a major problem. As this trend is expected to continue in a more pronounced manner, there is a need for higher resolution, higher sensitivity, and faster means of measuring stress (strain measuring means). Measuring of stress (strain), which can be carried out based on a distribution of stress (strain) inside a region as well as via a pinpoint precise measurement of a specific point, can provide a great amount of important information.

Various methods of measuring stress/strain have been proposed for required resolution. The simplest method is by the use of a strain gauge. Strain gauges can be roughly divided into mechanical and electric resistance-wire types. The mechanical strain gauge measures by converting the amount of strain into a physical quantity such as the twisting of an indicating needle. The electric resistance-wire type strain gauge is a converter element taking advantage of the property of a metallic wire whose resistance increases as it is extended. The surface acoustic wave method measures strain or stress by taking advantage of the fact that the speed of a surface acoustic wave that is created when an ultrasonic wave is impinged on a material surface differs depending on the magnitude of the strain or stress. The micro-Raman method is based on the principle that the peak position of the energy of scattered light emitted by a material upon laser light irradiation varies depending on the stress/strain.

According to a convergent-beam electron diffraction (CBED), a sample is irradiated with an electron beam converged to a small size, and the stress/strain in a specific direction is measured based on the changes in the diffraction pattern of the transmitted electron beam. The CBED method is described in JP Patent Publication (Kokai) No. 2000-65762, or Journal of Applied Physics, Vol. 32 (1993), p. 211, for example. The Fourier transform method utilizes the fact that the lattice interval of a crystal lattice image recorded on a high-resolution photograph taken by a transmission electron microscope (TEM) varies depending on the stress/strain. By cutting out a portion of the high-resolution photograph and subjecting it to fast Fourier transform (FFT), the lattice interval can be precisely determined. The Fourier transform method is described in JP Patent Publication (Kokai) No. 2000-65762, for example. The micro (nano) diffraction method utilizes the fact that the position of diffraction spots in an electron beam diffraction pattern obtained by TEM changes depending on the stress/strain of the sample. The method is called a micro diffraction method when the spot size of the irradiated electron beam is on the micrometer order and a nanodiffraction method when the spot size is on the nanometer order.

Examples of the means of observing a micro region of a sample include TEM, a scanning electron microscope (SEM), and a scanning transmission electron microscope (STEM). Electron beam scanning techniques are commonly employed in SEM and STEM. Both of them employ an irradiation lens system to focus an electron beam, which is then two-dimensionally scanned using a deflection coil. The signal intensity distributions of secondary electrons, reflected electrons, scattered electrons, and transmitted electrons that are produced in synchronism with the scan are displayed as images. The techniques for displaying the multiple items of information obtained from these signals simultaneously are also known. In recent years, techniques have also become known for analyzing the energy of a sample-transmitted electron beam and displaying, in synchronism with the scan, the intensity of an electron beam that has lost energy in the sample, or the intensity ratio of electron beams that have lost different energies.

A variety of means are known for detecting the two-dimensional position information of the electron beam, such as, for example, photosensitive films, TV cameras, SSCCD cameras, and imaging plates. These record the distribution of electron beam intensity as images. Examples of devices for detecting only the position of electron beam at high speed include two-dimensional position-sensitive detectors (PSD), micro channel plates (MCP), and position-sensitive photomultiplier tubes (PSPMT).

When measuring the stress/strain of a material, it is important to measure average quantities in a specific region. Furthermore, with the recent reduction in size of semiconductor elements, it is becoming increasingly necessary to measure local quantities at high spatial resolutions on the order of several nanometers. In addition to the measurement results concerning a specific location, there is also a growing need to obtain information about the spatial distribution of stress/strain. Of course, it is expected that two-dimensional mapping would take more measurement time than a measurement of a single point and would entail the problem of ensuring positional matching between the measurement result and the measurement location.

Hereafter, it will be analyzed whether or not the conventional measuring methods satisfy the required conditions for carrying out two-dimensional mapping of the stress/strain of a material. The conditions relate to spatial resolution, measurement time, degree of high-definition, measurement precision or sensitivity, and the positional matching between measurement results and measurement location.

Both mechanical and electric resistance-wire types of strain gauges are inexpensive, but their spatial resolution is on the millimeter order at most and are therefore only capable of providing average information concerning the inside of a particular region. Further, in order to measure a different point, the strain gauge must be re-positioned, which makes it difficult to carry out two-dimensional mapping of stress/strain. While the surface acoustic wave method is capable of measuring amorphous materials, their spatial resolution is on the order of 3-100 μm, which, though higher than the spatial resolution of the strain gauge, is not sufficient for the measurement of local stress/strain in a material. The microscopic Raman method is capable of measuring the distribution of stress/strain by scanning the material surface with a laser beam. However, this method cannot be easily applied to the field of semiconductors, because it is basically incompatible with metals and its spatial resolution is 3 μm or less, which, though relatively high, is still insufficient.

While the CBED method has a high spatial resolution—not more than 10 nm—and a high accuracy, it is mostly used for crystal samples with a simple structure because of limited analysis software resources. The measurement accuracy of the method is not more than 0.02%, which is the highest among the conventional methods. But this method is not suitable for mapping because it takes time to carry out an analysis of a single point and its positional matching with the measurement location is low. Furthermore, as the method employs an electron beam of an extremely high-order diffraction, it is subject to the influences of inelastic scattering in the sample, so that the signal amount can drastically decrease with increasing sample thickness. Thus, in order to obtain a satisfactory CBED pattern using a conventional electron microscope with an acceleration voltage of 200 to 300 kV, the sample thickness must be on the order of several tens of nanometers. A resultant problem, however, is that with the decrease in the thickness of the sample, the internal stress of the sample decreases to as much as one-hundredth or so of the original stress in the case of silicon, for example. Accordingly, there is the problem that the cause of the stress affecting the semiconductor device cannot be observed in the original form.

The Fourier transform method has spatial resolution of not more than 10 nm. It is effective in the two-dimensional measurement (mapping) because it processes FFT of small divided regions using a computer. Thanks to the improved computer performance, a high mapping-result definition and a high analysis position matching can be obtained. However, the analysis accuracy drops to about 5% if a spatial resolution of 10 nm or less is sought. The method also lacks real-time capability due to the many processes implemented after the taking of an electron microscopic picture.

The nano diffraction method achieves an improved resolution by focusing the irradiation electron beam and has spatial resolution of not more than 10 nm. Its measurement accuracy is not more than about 0.1%, which is second highest, after the CBED method. The nanodiffraction method is capable of two-dimensional mapping by electron beam scanning, but lacks real-time capability because, currently, it measures the position of a specific spot in an electron diffraction image taken by a TV camera by means of image processing techniques. A higher measurement position matching can be obtained by carrying out the nano diffraction method in an apparatus supportive of the positional comparison with a scan image, such as a STEM or SEM.

It is an object of the invention to solve the problems of the prior art and provide a method and apparatus for measuring the two-dimensional distribution of stress/strain at high resolution and sensitivity, with a high level of measurement position matching, and in a real-time manner.

SUMMARY OF THE INVENTION

The invention provides a method of measuring the physical properties of a micro region, comprising the steps of:

detecting the position of a specific diffraction spot of an electron beam diffraction image on a detection plane, the electron beam diffraction image being formed as a sample is scanned with an electron beam; and displaying a signal indicative of a change in the detected position of the specific diffraction spot on an image display apparatus in synchronism with electron beam scanning.

The invention provides a method of measuring the physical properties of a micro region, comprising the steps of:

detecting the interval or a change in the interval of a pair of diffraction spots of an electron beam diffraction image on a detection surface that are symmetrical with respect to a zero-order diffraction spot, the electron beam diffraction image being formed as a sample is scanned with an electron beam; and displaying a signal indicative of the detected interval or change in the interval of the pair of diffraction spots on an image display apparatus in synchronism with electron beam scanning.

The invention provides an apparatus for measuring the physical properties of a micro region, the apparatus comprising:

a condenser lens system for irradiating a sample with an accelerated electron beam;

an electron-beam deflecting means for controlling the position of the irradiation of the sample with the electron beam;

an objective lens for forming an electron beam diffraction image of the sample;

a focusing lens system for magnifying the electron beam diffraction image;

a two-dimensional electron detector for detecting a specific diffraction spot of the electron beam diffraction image magnified by the focusing lens system and then outputting a signal that depends on the detected diffraction spot position; and an image display apparatus for displaying an output signal from the two-dimensional electron detector or a signal produced on the basis thereof.

By these features, the stress/strain in a sample can be measured by a nano diffraction method. By using a two-dimensional position-sensitive electron detector as a two-dimensional electron detector, the stress/strain in a sample can be measured by a nano diffraction method at high speed.

The output signal from the two-dimensional electron detector or the signal produced on the basis thereof may be one or a combination of a signal $V_X$ indicating the displacement of the detected diffraction spot position in a predetermined direction (X-direction), a signal $V_Y$ indicating the displacement of the detected diffraction spot position in a direction (Y-direction) substantially perpendicular to the X-direction, a mean square of these signals ($\sqrt{(V_X^2+V_Y^2)}$), and an a tan ($V_Y/V_X$). This feature allows the X- and Y-components of the stress/strain, their composed component, and their directions to be displayed two-dimensionally.

The output signal from the two-dimensional electron detector or the signal produced on the basis thereof may be displayed on the image display apparatus in synchronism with the scanning of the sample with the electron beam by the electron beam deflecting means. In this way, the distribution of the stress/strain in the sample can be displayed two-dimensionally.

The invention provides an apparatus for measuring the physical properties of a micro region, the apparatus comprising:

a condenser lens system for irradiating a sample with an accelerated electron beam;

an electron beam deflecting means for controlling the position of the irradiation of the sample with the electron beam;

an objective lens for forming an electron beam diffraction image of the sample;

a focusing lens system for magnifying the electron beam diffraction image;

a first and a second two-dimensional electron detector each for detecting a pair of diffraction spots of the electron beam diffraction image magnified by the focusing lens system that are symmetrical with respect to a zero-order diffraction spot, and then outputting a signal that is dependent on the detected position of the diffraction spot;

a calculation means for calculating the interval or a change in the interval between the diffraction spot detected by the first two-dimensional electron detector and the diffraction spot detected by the second two-dimensional electron detector; and an image display apparatus for displaying a signal indicating the interval or change in the interval of the diffraction spots calculated by the calculation means in synchronism with the scanning of the sample with the electron beam by the electron beam deflection means.

By these features, the diffraction spots symmetrically positioned with respect to the zero-order transmitted electron beam can be respectively measured by independent two-dimensional position-sensitive electron detectors. Thus, even if the position of the zero-order transmitted electron beam is varied during electron beam scanning, the variation can be canceled so that the accuracy of measurement of the stress/strain can be improved.

The focusing lens system preferably includes the function of changing the magnification ratio of the electron beam diffraction image. The apparatus preferably comprises means for changing the relative angle between the first and the second two-dimensional electron detector and the electron beam diffraction image. In this way, the diffraction spots can be positioned easily. By varying the lens current in the focusing lens system and thereby changing the magnification ratio of the electron beam diffraction image as desired, the stress/strain can be measured regardless of the sample. Further, by allowing the relative angle between the electron diffraction image and the two-dimensional position-sensitive electron detector to be variable by varying the lens current in the focusing lens system or by rotating the two-dimensional position-sensitive electron detector, the stress/strain can be measured regardless of the direction of the sample.

The micro-region physical property measuring apparatus preferably comprises a diffraction spot selection aperture in front of the two-dimensional position-sensitive electron detector. The aperture selectively allows the passage of a specific diffraction spot of the electron beam diffraction image. By these features, the stress/strain in a specific direction only can be extracted and measured.

The micro-region physical property measuring apparatus may further comprise a second electron beam deflecting means disposed between the objective lens and the two-dimensional electron detector. By employing the second electron beam deflecting means, the position of the electron beam diffraction pattern can be adjusted and a specific electron beam diffraction spot can be allowed to pass through the aperture. These features allow the stress/strain to be easily measured.

The electron beam deflecting means for controlling the position of the irradiation of the sample with the electron beam and the second electron beam deflecting means may be driven in synchronism. This feature allows the position of the zero-order transmitted electron beam to be made substantially uniform regardless of electron beam scanning. Thus, the accuracy of measurement of the stress/strain can be improved. Specifically, two electron beam deflecting means are electrically connected in series, and the deflection amount of the second electron beam deflecting means is adjusted such that the position of the zero-order diffraction spot does not vary when the sample is scanned with the electron beam.

The focusing lens system located below the objective lens preferably comprises an electric lens system in at least two stages. This feature allows the diffraction image plane of the objective lens to be accurately projected on the two-dimensional position-sensitive electron detector plane in a magnified form. Thus, the position of the zero-order transmitted electron beam can be made substantially uniform regardless of electron beam scanning, thus improving the accuracy of measurement of stress/strain.

The micro-region physical property measuring apparatus preferably comprises a detector for detecting a secondary electron emitted by the sample, a reflected electron, a scattered electron, and/or a transmitted electron. An output signal from the two-dimensional electron detector or a signal produced on the basis thereof is displayed on the image display apparatus together with a signal from the detector for secondary electrons or the like in synchronism with the scanning of the sample with the electron beam by the electron beam deflection means. By thus displaying the signal from the two-dimensional position-sensitive electron detector in synchronism with the form information (such as a secondary electron image, a transmitted image, or a scattered image) about the sample included in the micro-region physical property measuring apparatus, the positional matching between the measurement result and the measurement location can be improved.

The micro-region physical property measuring apparatus preferably comprises a detector for detecting a secondary electron emitted by the sample, a reflected electron, a scattered electron, and/or a transmitted electron. The signal indicating the interval or change in the interval of the diffraction spots calculated by the calculation means is displayed on the image display apparatus together with a signal from the detector for secondary electrons or the like in synchronism with the scanning of the sample with the electron beam by the electron beam deflection means. These features allow the positional matching between the measurement result and the measurement location to be improved.

BRIEF DESCRIPTION OF THE DRAWINGS

FIG. 9 shows a block diagram of a micro-region physical property measuring apparatus capable of simultaneously displaying secondary electrons, transmitted electrons, scattered electrons, and so on.

BEST MODE FOR CARRYING OUT THE INVENTION

Figure 1:
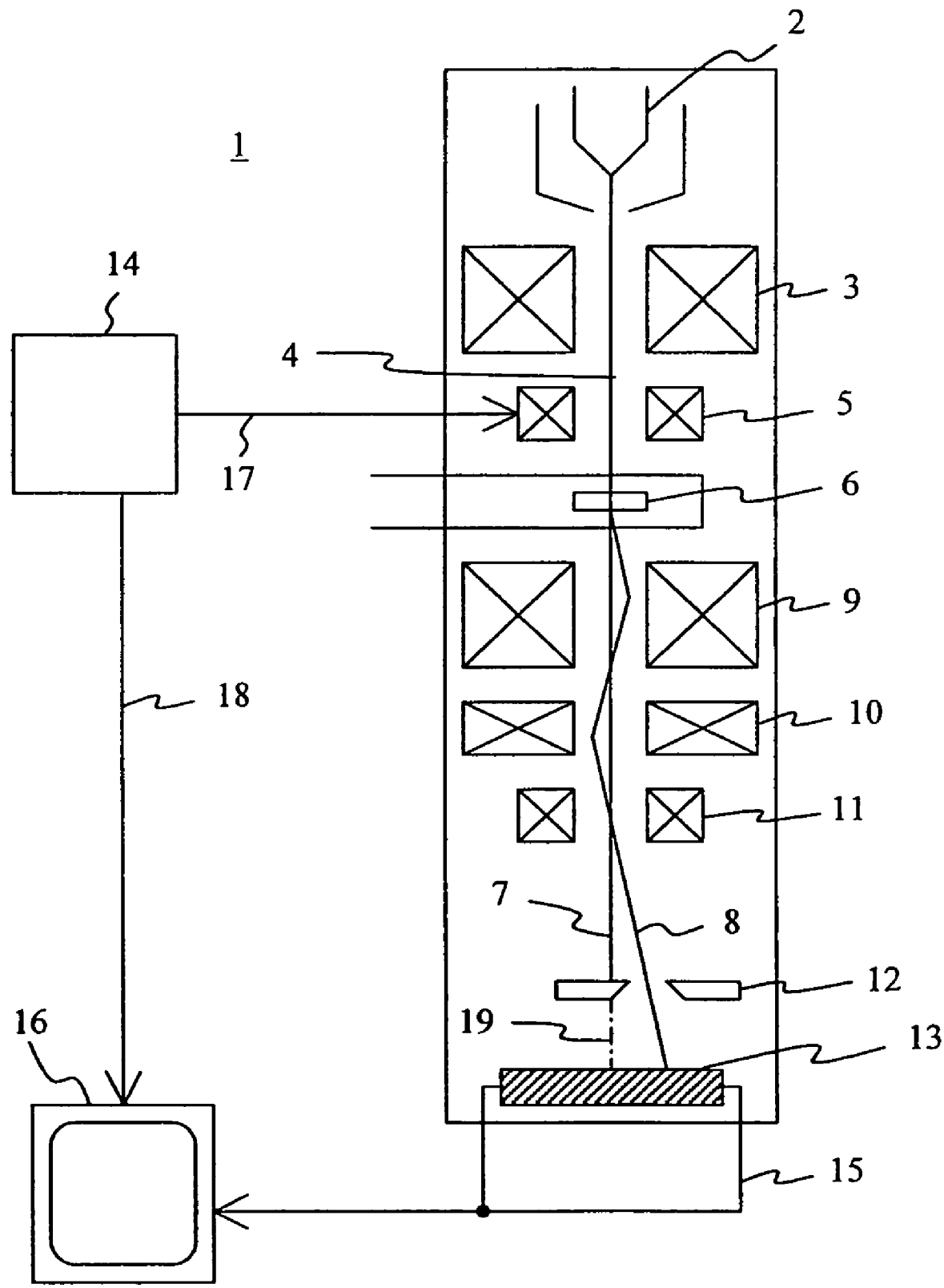
FIG. 1 shows a block diagram of an embodiment of a micro-region physical property measuring apparatus according to the invention, and a micro-region physical property measuring method employing the apparatus.

Hereafter, embodiments of the invention will be described by referring to the drawings.

FIG. 1 shows a block diagram of an example of a micro-region physical property measuring apparatus 1 according to the invention. An electron beam 4 emitted by an electron gun 2 is focused by a focusing lens 3 (part of a condenser lens system) and then a sample 6 is irradiated therewith. A deflection system control apparatus 14 produces a deflection system control signal 17 to control the deflection intensity of an irradiation deflection system 5 and thereby determine the position of the irradiating electron beam 4 on the sample 6. The electron beam transmitted by the sample 6 becomes a transmission electron beam 7 reflecting the structure of the sample 6 and a diffracted electron beam 8. The respective beams are magnified by an objective lens 9 and a projection lens 10 to an appropriate magnification ratio. Of a plurality of diffracted electron beams 8, only a specific diffraction spot passes through a diffraction spot selection aperture 12 and arrives onto a two-dimensional position-sensitive electron detector (to be hereafter referred to as a PSD) 13. The diffraction spot that is incident on the PSD 13 can be selected by adjusting the position of the diffraction spot selection aperture 12. The diffraction spot selection aperture 12 may be fixed either on the mirror cylinder of the micro-region physical property measuring apparatus 1 or on the PSD 13. It is also possible to fine-adjust the positional relationship of the diffraction spot selection aperture 12 and the diffracted electron beam 8 electrically by means of an intermediate deflection system 11.

The sample 6 is irradiated with the irradiation electron beam 4 such that the beam is converged to a small region with the beam's parallelism maintained as much as possible. When the irradiation electron beam 4 is converged to a size on nanometer order, the condition is called nano diffraction.

The PSD 13 outputs the location of the PSD where the diffracted electron beam 8 is incident as a voltage value. It outputs different voltage values for different locations of the arrival of the diffracted electron beam 8. The greater the location of arrival from an initial value, a more greatly different voltage value is outputted as a two-dimensional position signal 15. The thus obtained two-dimensional position signal 15 is displayed on the image display apparatus 16 as a luminance signal. The deflection system control signal 17 from the deflection system control apparatus 14 is outputted such that a rectangle region on the sample 6 is sequentially scanned. By using a deflection system synchronizing signal 18 synchronized with the sequential scan, the two-dimensional position signal 15 is displayed on the image display apparatus 16 in such a manner as to correspond to the position of the sample 6.

If the sample 6 has a uniform structure, the two-dimensional position signal 15 from the PSD 13 assumes a uniform value no matter where the irradiation electron beam 4 passes through the sample 6. Namely, an image with a uniform contrast is displayed on the image display apparatus 16. If in a region of the sample 6 the lattice interval is varied due to stress/strain, the angle of diffraction of the diffracted electron beam 8 is varied only when it scans that region. As a result, the position of the diffracted electron beam 8 on the PSD 13 changes, with the result that the voltage value of the two-dimensional position signal 15 is changed. Thus, on the image display apparatus 16, the regions of the sample 6 where stress/strain exists are provided with different contrasts from those of the other regions. It is therefore possible to display the distribution of stress/strain in the sample 6 on the image display apparatus 16. The voltage values of the two-dimensional position signal 15 from the PSD 13 may be converted into colors according to an appropriate rule and then displayed on the image display apparatus 16, so that the distribution of stress/strain of the sample can be displayed on the image display apparatus 16 in different colors.

Figure 2:
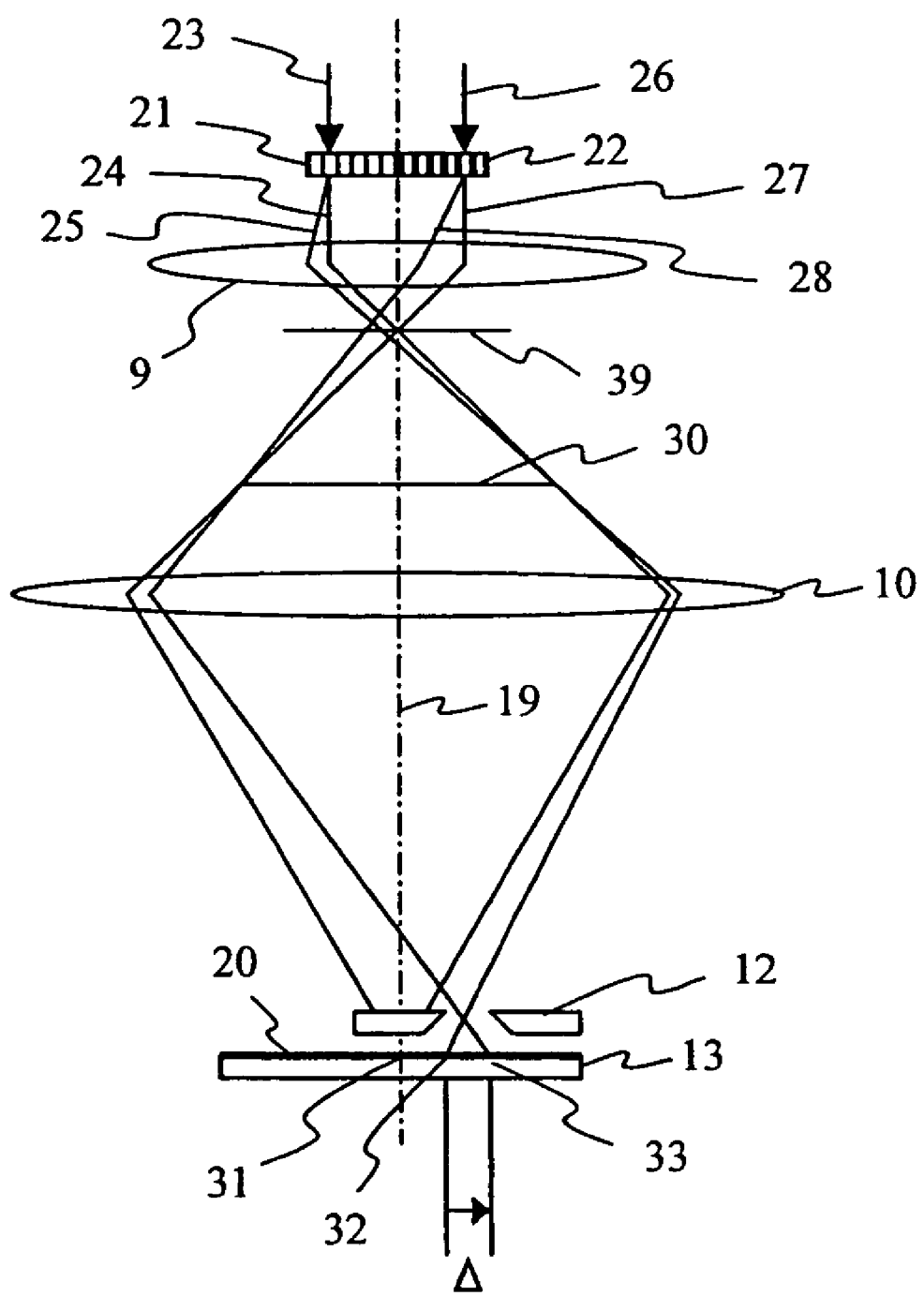
FIG. 2 shows the principle of measuring stress/strain based on nano diffraction.
Figure 3:
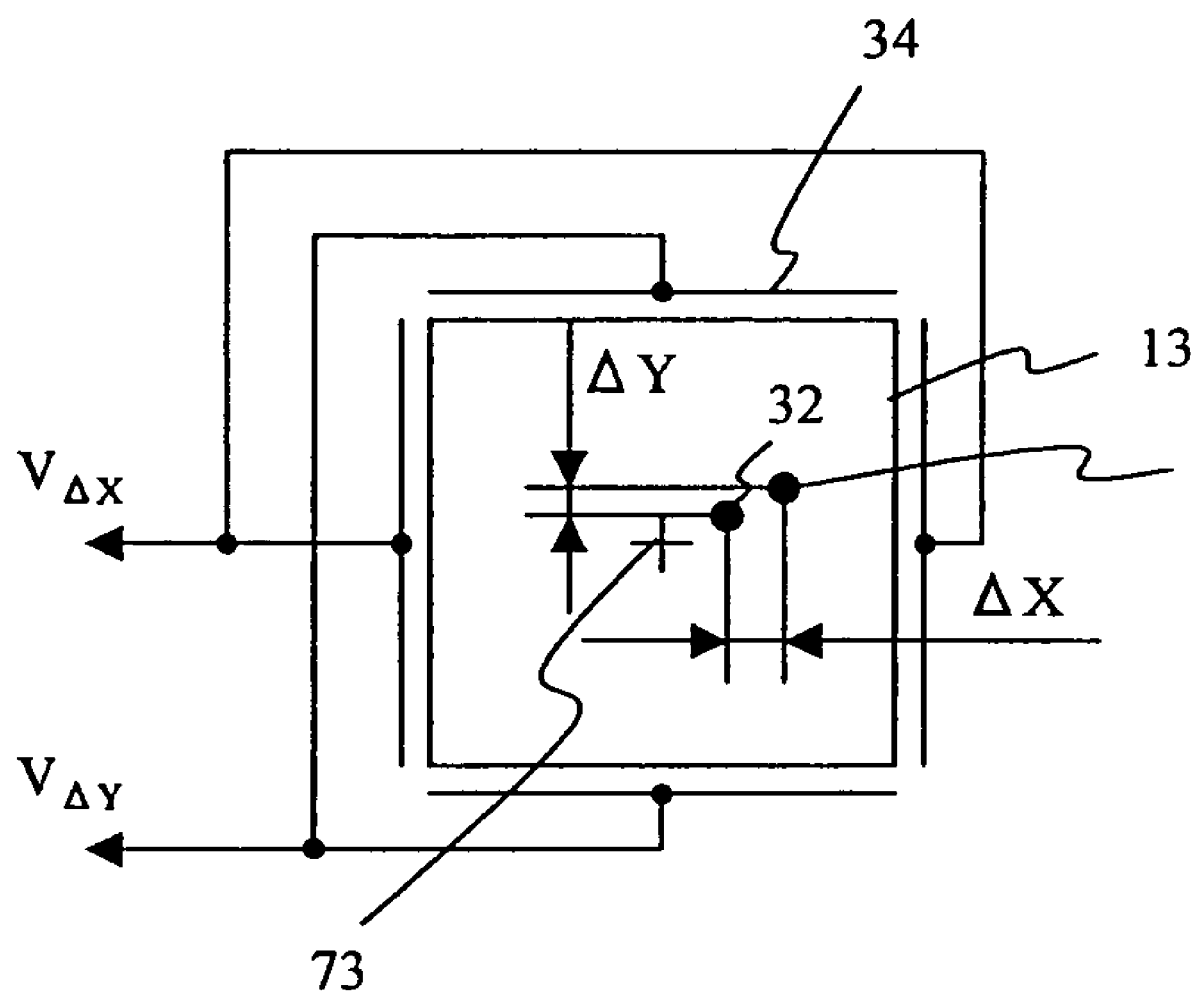
FIG. 3 is a drawing for the explanation of an output on a PSD.

Hereafter the principle of measuring stress/strain based on nano diffraction will be described by referring to the drawings. A light beam will be described by referring to FIG. 2, and the output of the PSD 13 on which an electron beam is incident will be described by referring to FIG. 3. Assume now that there are two regions 21 and 22 in the sample 6 that have different lattice intervals due to stress/strain. An electron beam 23 irradiating the region 21 of the sample is separated into a zero-order transmission wave 24 and a diffraction wave 25. The zero-order transmission wave 24 is guided by the objective lens 9 and the projection lens 10 and then arrives at a point 31 of intersection of the PSD 13 and the optical axis 19. The diffraction wave 25 arrives at a different location 32. On the other hand, an electron beam 26 irradiating the region 22 of the sample is also separated into a zero-order transmission wave 27 and a diffraction wave 28. The zero-order transmission wave 27 and the diffraction wave 28 arrive at the point 31 of intersection of the PSD 13 and the optical axis 19 and a different location 33, respectively. As the lattice intervals of the regions 21 and 22 are different, the angle of diffraction of the diffraction wave 28 is different from that of the diffraction wave 25, and the location 33 is different from the location 32. On the PSD 13 is focused a magnified pattern of a focal plane 29 behind the objective lens 9, and each of the transmission waves 24 and 27 and the diffraction waves 25 and 28 is focused to a single point. The spot (zero-order diffraction spot) 31 of the transmission wave is blocked by an aperture 12, and only the spots 32 and 33 of the diffraction waves arrive at the PSD 13. Numeral 30 designates an image plane of the objective lens 9.

The surface of the PSD 13 is coated with a fluorescent substance 20 so that the incident electron beam can be converted into light for detection. An electrode 34 outputs the point of arrival of the electron beam in the plane of the PSD 13 as a voltage proportional to the distance, both in X- and Y-directions simultaneously, from a predetermined origin 73. When the differences in voltages outputted at the respective spot positions are $V_{\Delta X}$ and $V_{\Delta Y}$, the voltage V corresponding to the distance $\Delta$ of displacement of the actual spot, $\Delta = \sqrt{(\Delta X^2 + \Delta Y^2)}$, is given by $V = \sqrt{(V_{\Delta X}^2 + V_{\Delta Y}^2)}$, and thus $\Delta$ is proportional to V. By determining the proportionality coefficient between $\Delta$ and V in advance, the distance of displacement $\Delta$ can be determined based on the voltages $V_{\Delta X}$ and $V_{AY}$. The distance between a diffraction wave spot and the zero-order spot 31 is inversely proportional to the lattice coefficient. Thus, the spot 33 of the diffraction wave is incident farther away from the zero-order spot with a decreasing lattice interval, and closer to the zero-order spot with an increasing lattice interval. By utilizing this relationship, the amount of change in the lattice interval can be measured based on the distance $\Delta$ of displacement of the diffraction spot 33.

When the acceleration voltage of the micro-region physical property measuring apparatus 1 is 200 kV and the fundamental lattice interval of the sample 6 is 0.2 nm, the angle of diffraction is about 12.5 mrad. When the camera length on the PSD 13 is 2 m, the diffraction spot on the PSD 13 is located 25 mm away from the zero-order spot. Assuming the lattice interval has varied by 1% due to stress/strain and has become 0.202 nm, the distance between the diffraction spot and the zero-order spot on the PSD 13 would be 24.75 mm, which is represents displacement of 0.25 mm. In light of the fact that the positional resolution of the current PSD 13 and the eventual resolution determined by the particle size of the fluorescent substance 20, for example, are not more than 10 μm, the detection of the above displacement is easy, and an eventual stress/strain resolution of not more than 0.1% can be easily achieved.

The output of the two-dimensional position signal 15 from the PSD 13 has a slight time delay but could be called a roughly real-time signal. Thus, by increasing the speed of the sequential scan of the irradiation electron beam 4, the stress/strain distribution can be displayed in real time.

Figure 4:
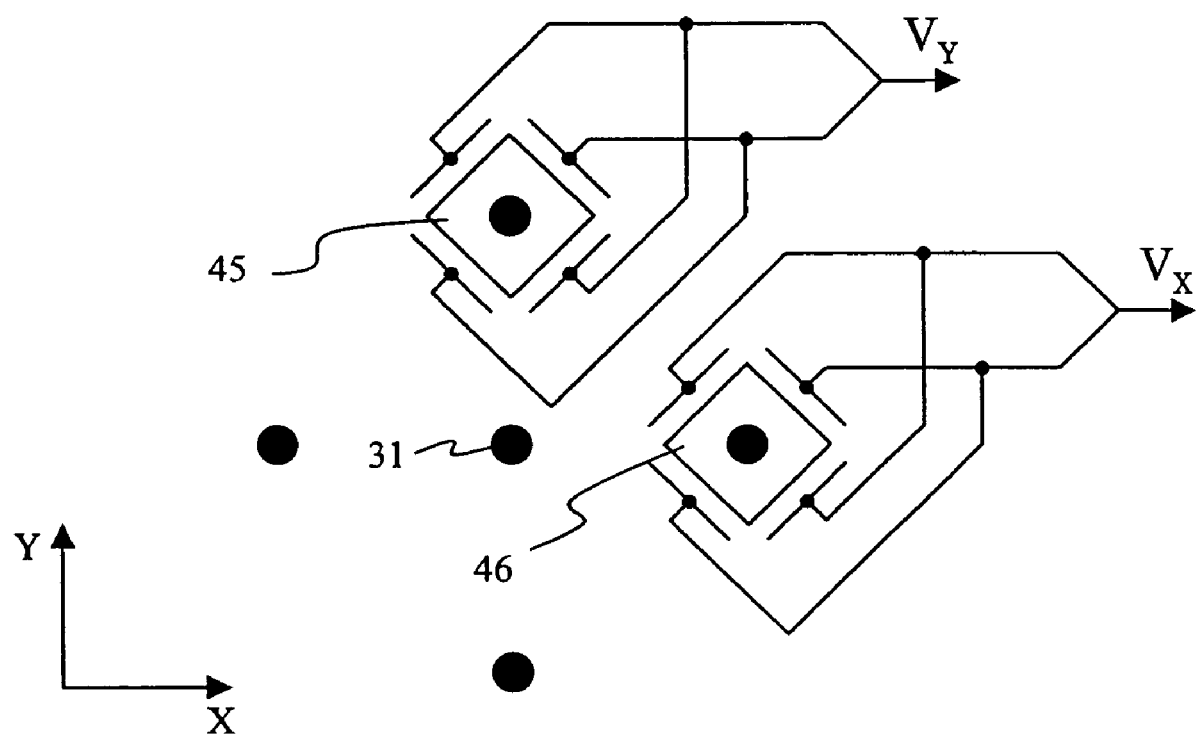
FIG. 4 is a drawing for the explanation of a method of measuring stress/strain in X- and Y-directions.

Within the sample plane, stress/strain does not exist in one direction, and therefore it is necessary to measure both in X- and Y-directions. By combining PSDs 45 and 46 as shown in FIG. 4, the X-direction ($V_X$) and the Y-direction ($V_Y$) can be independently measured. In the illustrated example, when XY coordinate axes with an origin located at the zero-order spot 31 is considered, the position displacement of a specific diffraction spot on the X-axis is detected by the PSD 46 and the position displacement of a specific diffraction spot on the Y-axis is detected by the PSD 45. As the diffraction spots to be detected by the two PSDs 45 and 46, it is desirable to chose diffraction spots in directions that are as much perpendicular as possible with one another. However, diffractions spots that are not perpendicular to one another pose no practical problems as long as their direction components are known.

Suppose that a diffraction spot from a sample region without stress/strain is incident on each origin of the PSDs 45 and 46 (V=0). When the composed outputs of the PSDs 46 and 45 are $V_X$ and $V_Y$, respectively, each PSD detecting the distance of displacement of a diffraction spot corresponding to a measured location of the sample from the origin, the total amount of stress/strain at the measured location can be determined by $\sqrt{(V_X^2+V_Y^2)}$. The direction of stress/strain is expressed by a tan $(V_Y/V_X)$. As the value of a tan $(V_Y/V_X)$ cannot be distinguished if both X and Y increase or decrease, the output should preferably be multiplied by the sign of $V_X$ (or $V_Y$). While these output values can be processed in real time by designing the electric circuitry accordingly, only VY and YX may be recorded at first and later analyzed by a computer, for example.

In the present example, analysis is carried out using one composed output from the PSD 45 and one composed output from the PSD 46. However, stress/strain may be analyzed by using the raw signals obtained from the individual PSDs, i.e., the two-component output from the PSD 45 and another two-component output from the PSD 46 if the relationship between the coordinates of the diffraction pattern and those in each PSD is known.

While in the above description it was assumed that the position of the zero-order diffraction spot does not change, it could change in reality. Hereafter, problems that could be encountered in such a situation and ways of dealing with them will be described.

Figure 5:
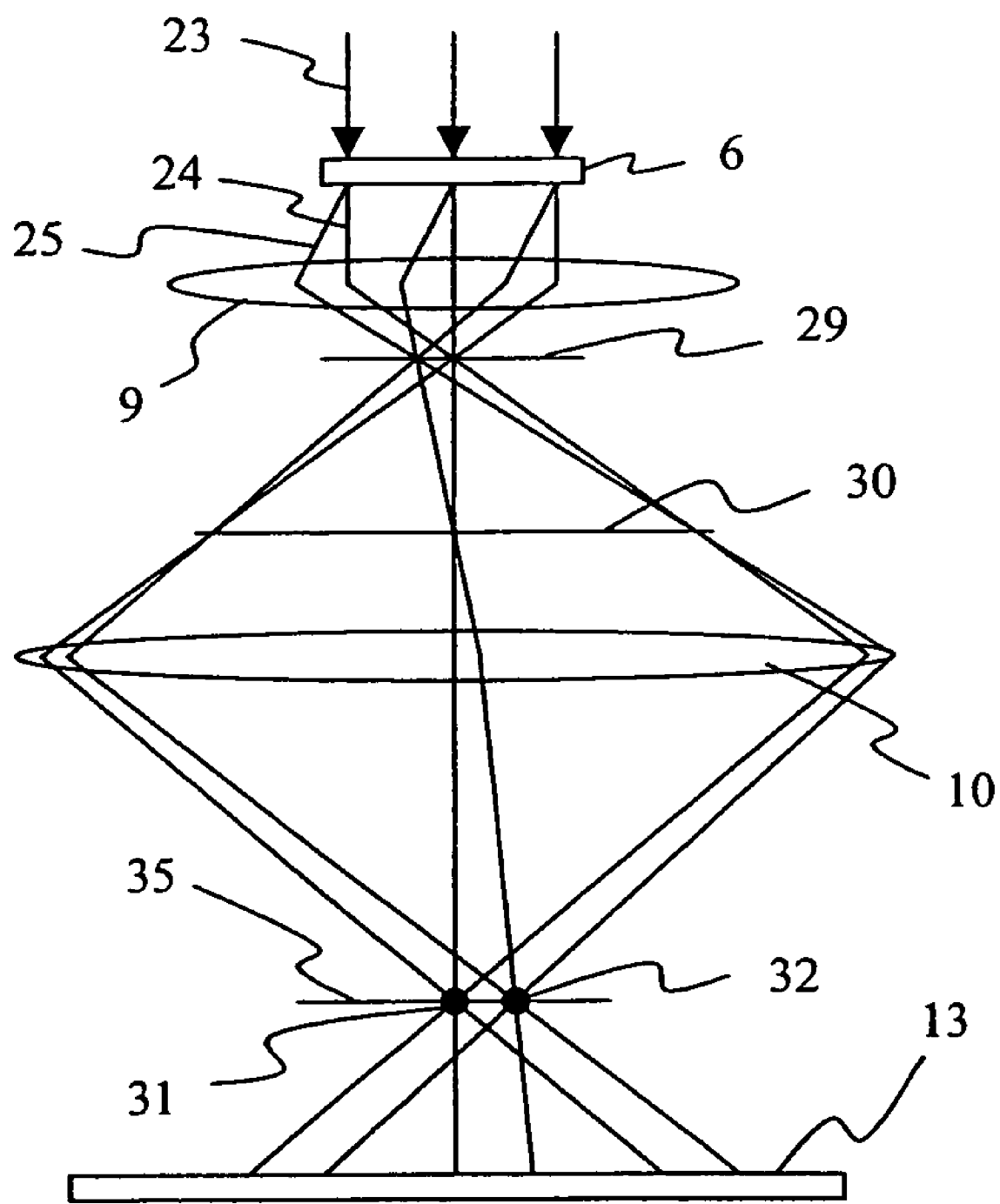
FIG. 5 is a drawing for the explanation of a case where no diffraction image is focused on the PSD.

One possible cause of the change in the position of the zero-order diffraction spot is the failure of the projection lens 10 to accurately project the focal plane 29 behind the objective lens 9 on the PSD 13, as shown in FIG. 5. When the electron beam 23 scans the sample 6, the diffraction images 31 and 32 produced by the projection lens 10 do not shift on the diffraction image plane 35 of the projection lens, but they do on the PSD 13, which is not coincident with the diffraction image plane 35. In order to measure stress/strain, the amount of change of the distance from the zero-order spot 31 must be measured. Thus, if the zero-order spot 31 is shifted, the stress/strain cannot be accurately measured. Further, if the amount of displacement of the zero-order spot 31 is too great, a specific spot cannot be selected by the aperture 12.

Figure 6:
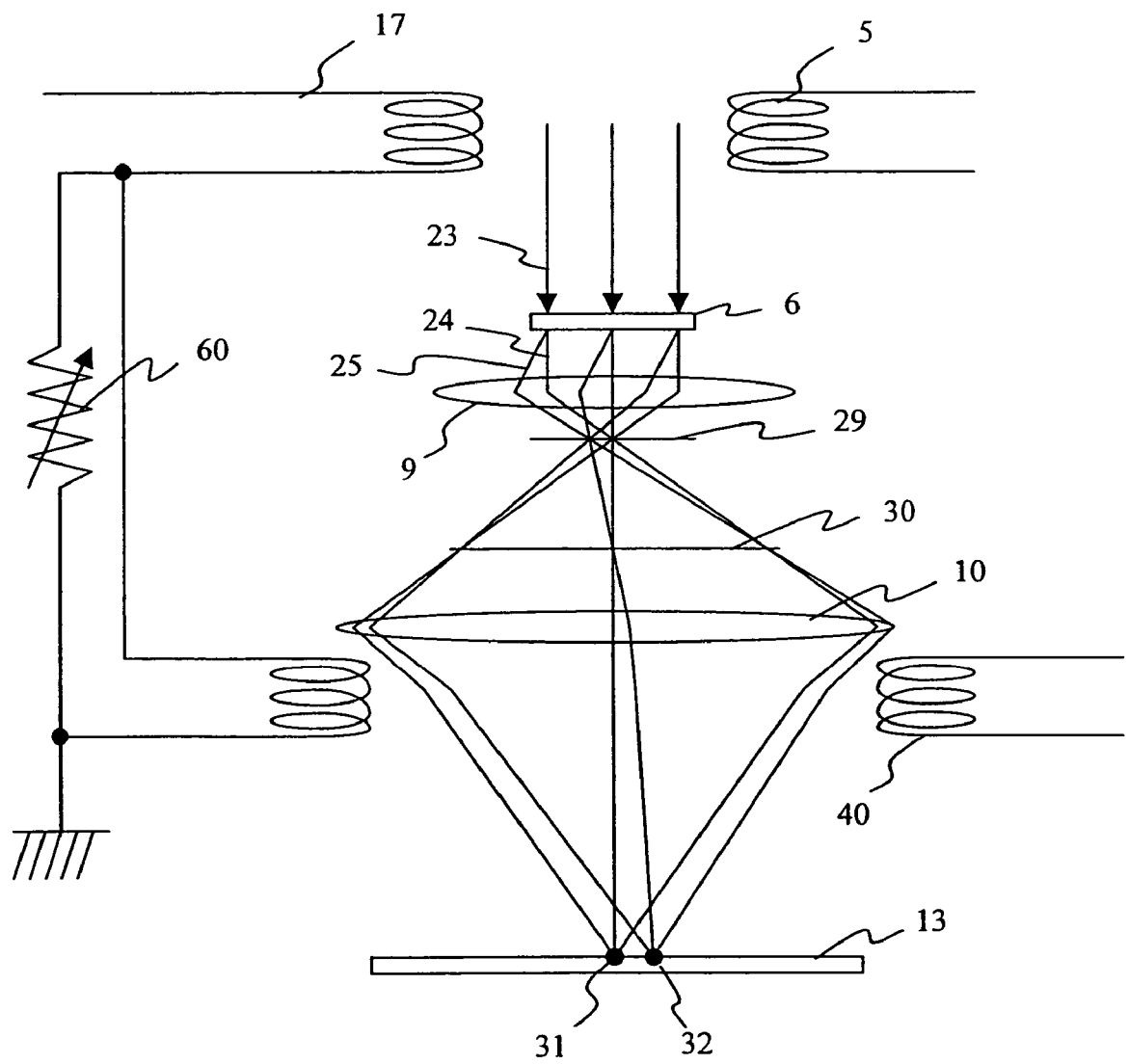
FIG. 6 shows the principle of a method of correcting the displacement of a diffraction spot by means of a correction electron beam deflection system.

FIG. 6 is a drawing for the description of an example of a method of correcting the displacement of the diffraction spot. According to this method, a corrective electron-beam deflection system 40 is provided near the projection lens 10 in order to correct the displacement of the diffraction spot. The corrective electron beam deflection system 40 is fed with an electric current proportional to the scan signal 17 by means of a signal 18 synchronized with the scan signal 17 for the irradiation electron beam 23. A very fast response can be obtained by connecting the corrective electron beam deflection system 40 in series with the irradiation deflection system 5 and adjusting the current with the number of turns of the coils or a variable resistor 60 in the corrective electron beam deflecting system 40. The variable resistor 60 is adjusted such that the zero-order spot 31 does not shift when the sample 6 is scanned with the irradiation electron beam 23.

Figure 7:
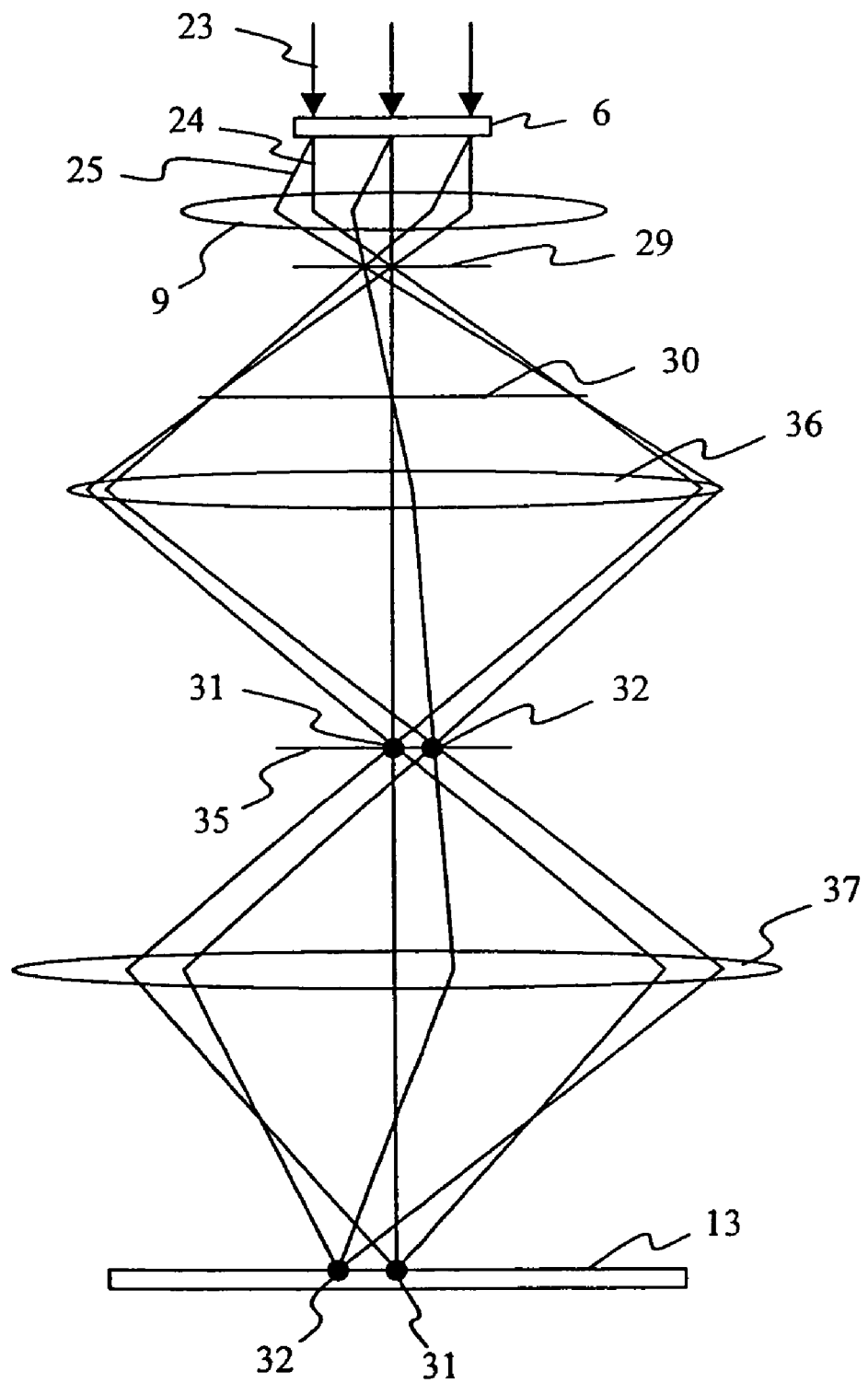
FIG. 7 shows the principle of a method of correcting the displacement of a diffraction spot by providing projection lenses in two stages.

FIG. 7 shows another means of avoiding the problems associated with the failure of the projection lens 10 to project the focal plane 29 behind the objective lens 9 accurately on the PSD 13. According to this method, projection lenses 36 and 37 are provided in two stages, and the diffraction pattern that appears on the focal plane 29 behind the objective lens 9 is projected on the PSD 13 as magnified. It goes without saying that there may be more than two stages of projection lenses. In this case, the magnification ratio can be varied based on the combination of the excitation currents supplied to the first projection lens 36 and the second projection lens 37, so that the accuracy of measurement of the diffraction spot on the PSD 13 can be varied. If the sample has small stress/strain, the stress/strain can be measured accurately by increasing the magnification ratio. Conversely, if the sample has large stress/strain, the overall distribution can be appropriately measured by lowering the magnification ratio.

Figure 8:
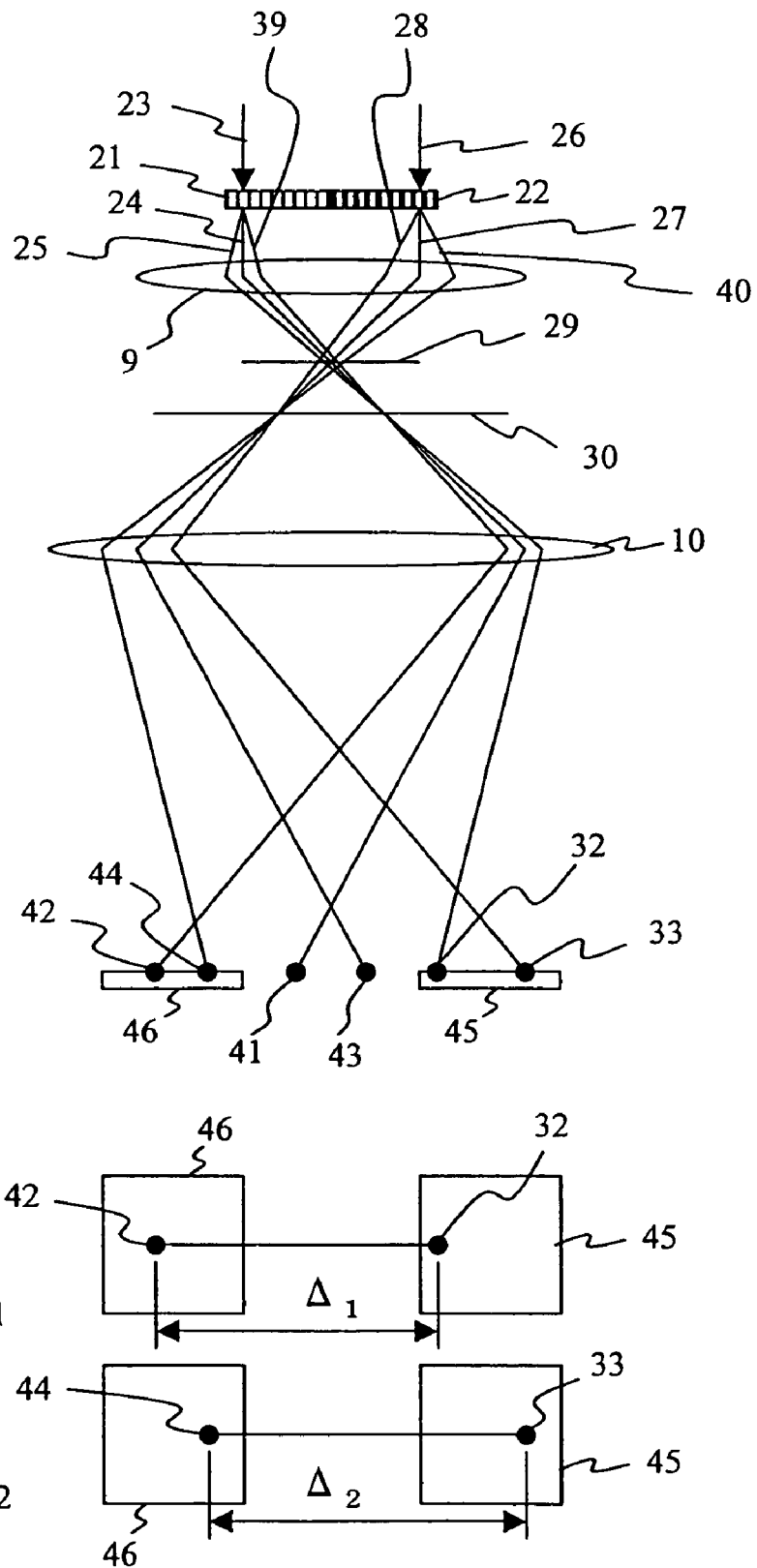
FIG. 8 shows the principle of a method of correcting the displacement of a diffraction spot by arranging two PSDs.

FIG. 8 shows another means of avoiding the problems associated with the failure of the projection lens 10 to accurately project the focal plane 29 behind the objective lens 9 on the PSD 13. Irradiation electron beams 23 and 26 incident on different regions 21 and 22 of a sample respectively are separated into transmitted electron beams 24 and 27 and diffracted electron beams, the latter in one direction, 25 and 28, and in another, symmetric direction, 39 and 40. The individual electron beams are focused by the objective lens 9 and the projective lens 10 into diffraction patterns.

The transmitted electron beams arrive at 41 and 43, the diffracted electron beams in one direction arrive at 32 and 33, and the diffracted electron beams in a symmetric direction arrive at 42 and 44. The diffraction spots 32 and 33 are detected by the first PSD 45, and the diffraction spots 42 and 44 are detected by the second PSD 46.

Assume that the positions of the diffraction spots 32 and 42 from the region 21 of the sample are measured by the first and second PSDs 45 and 46 to obtain an inter-spot distance $\Delta_1$. Further assume that the positions of the diffraction spots 33 and 44 from the region 22 of the sample are measured by the first and second PSDs 45 and 46 to obtain an inter-spot distance $\Delta_2$. If the value of $\Delta_1$ is taken as a reference, i.e., if it is assumed that the region 21 does not have any stress/strain, the amount of displacement of the diffraction spots in the region 22 can be expressed by $(\Delta_2-\Delta_1)/2$.

By developing this method further as described with reference to FIG. 4, the stress/strain components in the X- and Y-directions can be simultaneously measured. In that case, four PSDs would be required.

Thus far it has been described how it is possible to accurately measure stress/strain in the X- and Y-directions simultaneously by arranging two or four PSDs. The PSDs can be correctly arranged if the structure and orientation of the sample 6 and the angle of rotation of the image by the objective lens 9 and the projection lens 10 are known in advance. In general, however, these conditions are not known in many cases, and therefore a means is required for selecting a specific obtained electron diffraction spot.

The means for selecting one of the diffraction spots can be easily provided by the diffraction selection aperture 12, as shown in FIG. 1. However, in order to select a plurality of diffraction spots and detect them on separate PSDs, the direction and the distance from the zero-order diffraction spot must be adjusted. The direction can be adjusted by rotating a PSD, for example. In this case, the diffraction spot aperture can be fixed on each of a plurality of PSDs. In another example, the diffraction pattern can be rotated to take advantage of the property of an electric lens in which the image is rotated by an amount proportional to excitation. In the latter case, the projection lenses should preferably be employed in multiple stages as shown in FIG. 7 in order to enhance the degree of freedom.

In order to adjust the distance from the zero-order diffraction spot, a means for changing the magnification ratio (camera length) of the diffraction spot must be provided. This can be easily achieved by changing the excitation of the projection lens. Many of the current general-purpose TEMs include two stages of intermediate lenses and two stages of projection lenses. They can achieve a wide range of camera-length variation and arbitrary rotation directions simultaneously, and are capable of measuring the stress/strain distribution of any given crystal samples.

Figure 9:
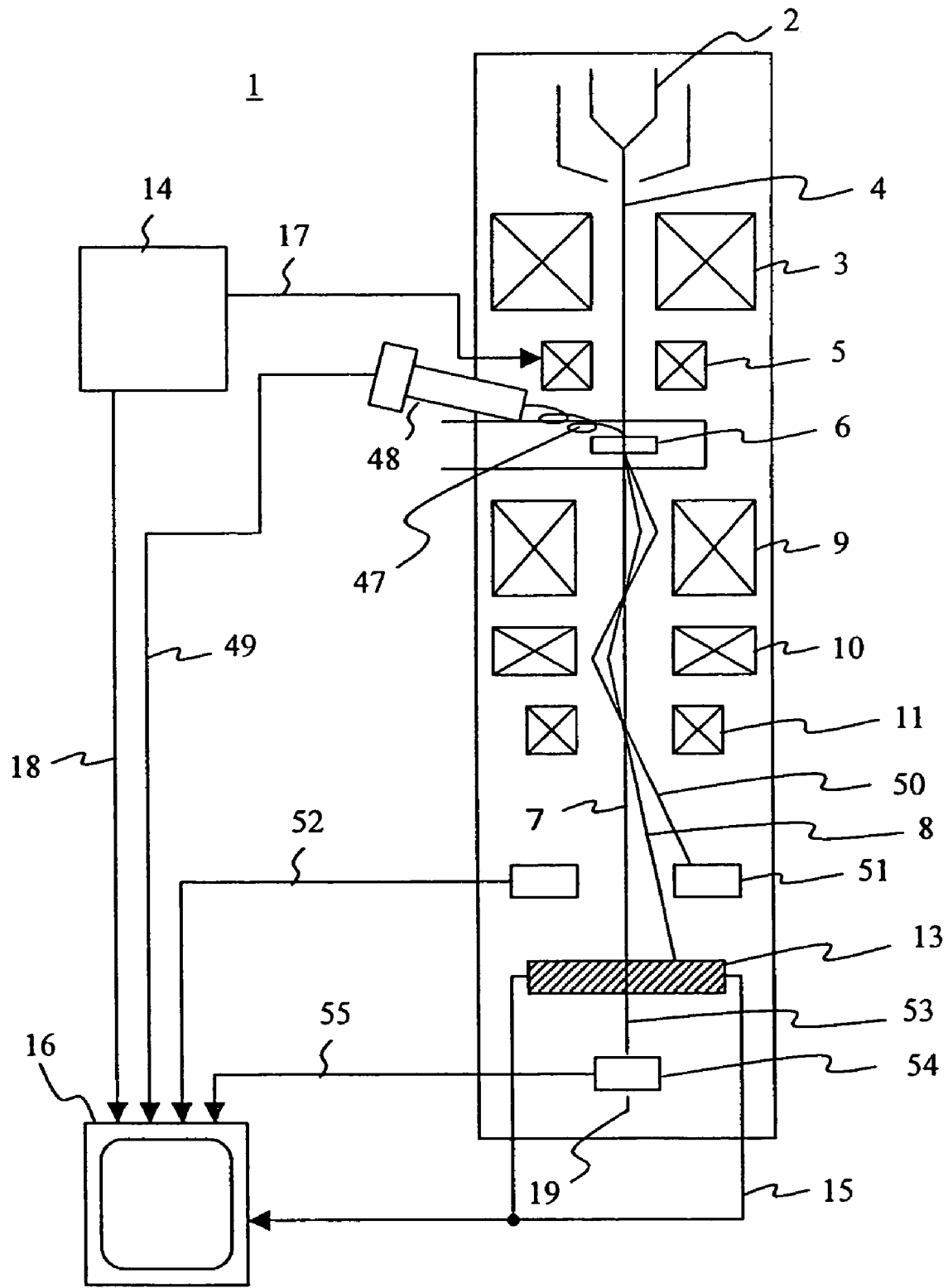

FIG. 9 shows a block diagram of an example of the micro-region physical property measuring apparatus capable of displaying the stress/strain distribution simultaneously with a secondary electron image, scattered electron image, and/or transmission electron image of a sample.

A secondary electron detector 48 detects a secondary electron 47 emitted from the sample. A scattered electron detector 51 detects a scattered electron 50 scattered by the sample 6. A transmission electron detector 54 detects a transmission electron 53 transmitted by the sample. These signals include shape information about the sample 6 and, if displayed simultaneously with the stress/strain distribution, can provide more significant information. This can be easily achieved by feeding a secondary electron signal 49, a scattered electron signal 52, and a transmission electron signal 55 into the image display apparatus 16 simultaneously with the two-dimensional position signal 15 indicating the magnitude of the stress/strain and in synchronism with the deflection system synchronization signal 18 from the deflection system control apparatus 14. Thus, the positional matching between the measurement result and the measurement location can be improved.

By providing the TEM, STEM, or SEM with an energy dispersion X-ray spectroscopic analyzer (EDX) or an energy loss spectroscopic analyzer (EELS), elemental analysis or element-distribution display can be achieved. Simultaneous display with a signal for evaluating the physical properties of the sample, such as cathode luminescence or reflection electrons, can be easily achieved by the above-described means.

Figure 10:
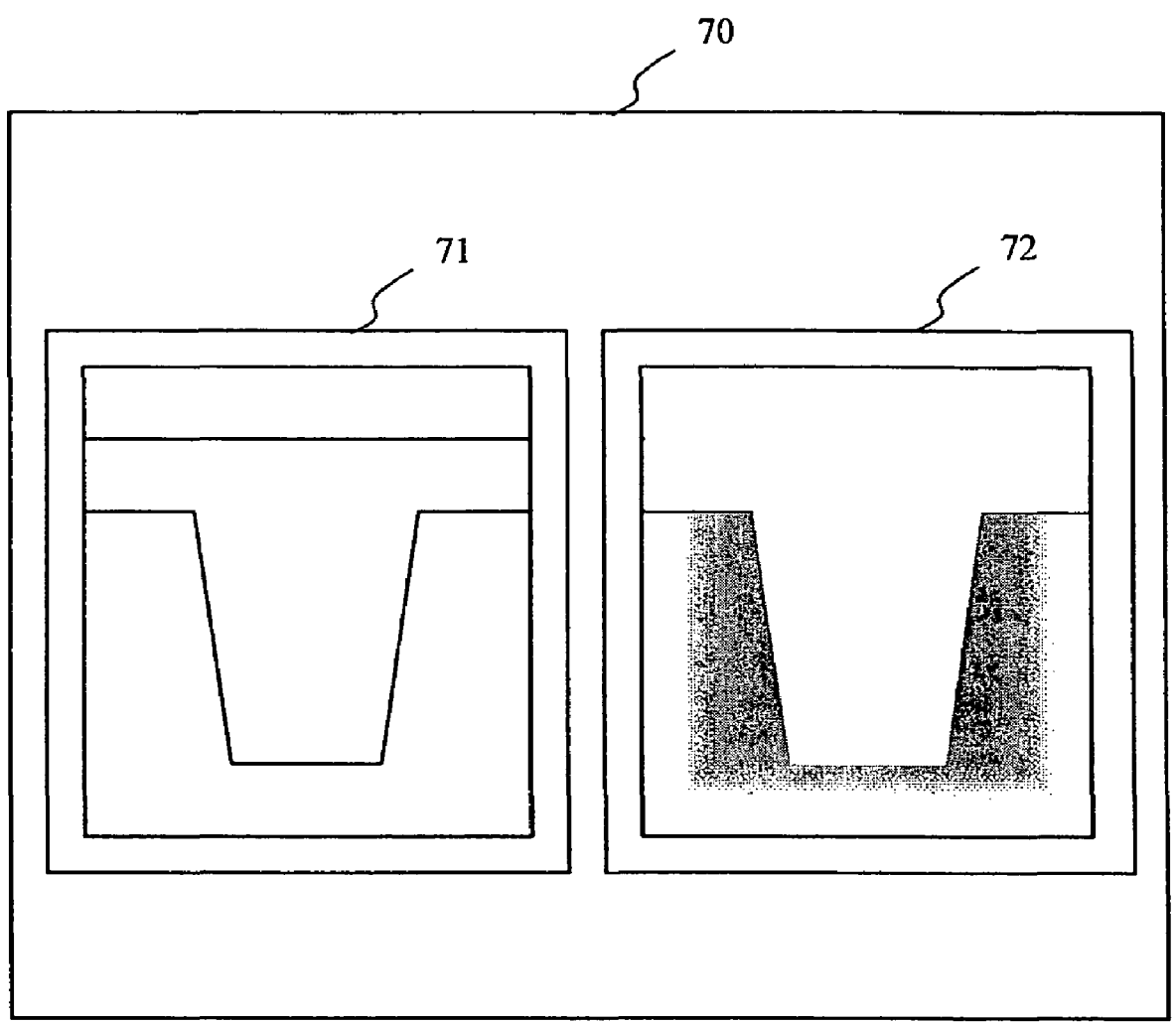
FIG. 10 shows an example of a display screen showing a secondary electron image, a transmitted electron image, and a scattered electron image of a sample simultaneously with the distribution of stress and strain.

FIG. 10 shows an example of the display screen showing the stress/strain distribution simultaneously with the secondary electron image, transmission electron image and/or scattered electron image of the sample. In the drawing, a secondary electron image 71 and a stress/strain distribution image 72 are displayed side by side on a display screen 70 of the image display apparatus 16.

Generally, the secondary electron signal 49 contains information about the surface or internal structure of the sample, the scattered electron signal 52 contains information about the constituent elements of the sample, and the transmission electron signal 55 contains information about defects in the sample, for example, in addition to the shape information. Accordingly, by displaying the secondary electron image 71 and the stress/strain distribution image 72 side by side, for example, the shape of the sample as well as its surface or internal structure can be associated with the position of stress/strain. Thus, information relating to whether stress/strain is concentrated at a broken or defective portion or at an interface with another structure, or concentrated in adjacent areas, and whether stress/strain varies sharply and how it is subsiding, for example, can be visualized.

INDUSTRIAL APPLICABILITY

Thus, in accordance with the invention, the two-dimensional distribution of stress (strain) in a sample can be displayed in real time at high spatial resolution and sensitivity and with a high level of measurement position matching.

The invention claimed is:

1. An apparatus for measuring the physical properties of a micro region, the apparatus comprising:
    a condenser lens system for irradiating a sample with an accelerated electron beam;
    an electron-beam deflecting means for controlling the position of the irradiation of the sample with the electron beam;
    an objective lens for forming an electron beam diffraction image of the sample;
    a focusing lens system for magnifying the electron beam diffraction image;
    a two-dimensional electron detector for outputting a signal pertaining to a position of a specific diffraction spot of the electron beam diffraction image magnified by the focusing lens system; and
    an image display apparatus for displaying an output signal from the two-dimensional electron detector, corresponding to a displacement distance of the specific diffraction spot on the detection plane in synchronism with electron-beam deflection by the electron-beam deflecting means.

2. The micro-region physical properties measuring apparatus according to claim 1, wherein the output signal from the two-dimensional electron detector is one or a combination of a signal VX indicating the displacement of the detected diffraction spot position in a predetermined direction (X-direction), a signal VY indicating the displacement of the detected diffraction spot position in a direction (Y-direction) substantially perpendicular to the X-direction, a mean square of these signals ($\sqrt{(V_X^2+V_Y^2)}$), and an atan ($V_Y/V_X$).

3. The micro-region physical properties measuring apparatus according to claim 2, wherein the output signal from the two-dimensional electron detector displayed on the image display apparatus in synchronism with the scanning of the sample with the electron beam by the electron beam deflecting means.

4. The micro-region physical properties measuring apparatus according to claim 1, wherein the output signal from the two-deminsional electron detector is displayed on the image display apparatus in synchronism with the scanning of the sample with the electron beam by the electron beam deflecting means.

5. The micro-region physical property measuring apparatus according to claim 4, further comprising a detector for detecting a secondary electron emitted by the sample, a reflected electron, a scattered electron, and/or a transmitted electron, wherein an output signal from the two-dimensional electron detector is displayed on the image display apparatus together with a signal from the detector in synchronism with the scanning of the sample with the electron beam by the electron beam deflection means.

6. The micro-region physical property measuring apparatus according to claim 1, further comprising a diffraction spot selection aperture that selectively allows the passage of a specific diffraction spot of the electron beam diffraction image.

7. The micro-region physical property measuring apparatus according to claim 1, further comprising a second electron beam deflecting means disposed between the objective lens and the two-dimensional electron detector.

8. The micro-region physical property measuring apparatus according to claim 7, further comprising a deflection system control unit for controlling the electron beam deflecting means for controlling the position of the irradiation of the sample with the electron beam and the second electron beam deflecting means so that deflection signals of the two electron beam deflecting means can be driven in synchronism.

9. The micro-region physical property measuring apparatus according to claim 1, wherein the focusing lens system comprises an electric lens system in at least two stages.

10. The micro-region physical property measuring apparatus according to claim 9, wherein the focusing lens system projects a diffraction image plane of the objective lens onto a detection plane of the two-dimensional electron detector.

11. A method of measuring the physical properties of a micro region, comprising the steps of:
  detecting the position of a specific diffraction spot of an electron beam diffraction image on a detection plane, the electron beam diffraction image being formed as a sample is scanned with an electron beam; and
  displaying a signal amount corresponding to a displacement distance of the specific diffraction spot on the detection plane, on an image display apparatus in synchronism with electron beam scanning.

* * * * *